(12) United States Patent
Jung et al.

(10) Patent No.: US 6,368,770 B1
(45) Date of Patent: Apr. 9, 2002

(54) PHOTORESIST MONOMERS, POLYMERS THEREOF, AND PHOTORESIST COMPOSITIONS CONTAINING THE SAME

(75) Inventors: Min Ho Jung; Jae Chang Jung; Geun Su Lee; Ki Ho Baik, all of Kyoungki-do (KR)

(73) Assignee: Hyundai Electronics Industries Co. Ltd. (KR)

( * ) Notice: Subject to any disclaimer, the term of this patent is extended or adjusted under 35 U.S.C. 154(b) by 0 days.

(21) Appl. No.: 09/621,125

(22) Filed: Jul. 21, 2000

(30) Foreign Application Priority Data

Jul. 30, 1999 (KR) .............................. 99-31302

(51) Int. Cl.[7] .............................. G03F 7/004
(52) U.S. Cl. .................. 430/270.1; 430/326; 430/913; 430/921; 560/120; 526/282
(58) Field of Search .............................. 430/270.1, 326, 430/913, 921; 526/282; 560/120

(56) References Cited

U.S. PATENT DOCUMENTS 6,140,015 A * 10/2000 Varanasi et al. ......... 430/281.1

6,200,731 B1 * 3/2001 Lee et al. ................ 430/270.1

FOREIGN PATENT DOCUMENTS

GB        2 345 285 A        7/2000

* cited by examiner

*Primary Examiner*—Rosemary Ashton
(74) *Attorney, Agent, or Firm*—Townsend and Townsend and Crew LLP

(57) ABSTRACT

The present invention provides a novel photoresist monomer, photoresist copolymer derived from the same, and the photoresist composition comprising the same. In particular, the present invention provides a photoresist monomer of the formula:

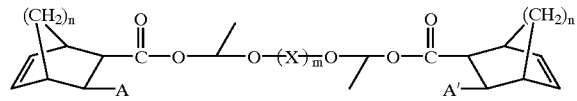

wherein, A, A', X, m and n are those defined herein. The photoresist composition of the present invention has an excellent etching and heat resistance, and enhances the resolution and profile of the photoresist film.

31 Claims, No Drawings

PHOTORESIST MONOMERS, POLYMERS THEREOF, AND PHOTORESIST COMPOSITIONS CONTAINING THE SAME

BACKGROUND OF THE INVENTION

1. Field of the Invention

The present invention relates to a photoresist monomer, polymers derived from the monomer, and photoresist compositions comprising the same. More specifically, the invention relates to a bis(norbornene carboxylate) and a bis(norbornene dicarboxylate) monomers comprising an acetal group, polymers derived from the same, and photoresist compositions comprising the same.

2. Description of the Background Art

Recently, chemical amplification type DUV photoresists have been investigated in order to achieve high sensitivity in minute image formation processes for preparing semiconductor devices. Such photoresists are prepared by blending a photoacid generator and matrix resin polymer having an acid labile group.

In the lithography process, resolution depends upon the wavelength of the light source—the shorter the wavelength, the more minute pattern can be formed.

Recently, chemical amplification type DUV photoresists have been investigated for achieving a high sensitivity in minute image formation processes for preparing semiconductor devices. Such photoresists are typically prepared by blending a photoacid generator and a matrix resin polymer having an acid labile group. The resolution of a lithography process depends, among others, on the wavelength of the light source, i.e., shorter the wavelength, smaller the pattern formation.

In general, a useful photoresist (hereinafter, abbreviated to as "PR") has a variety of desired characteristics, such as an excellent etching resistance, heat resistance and adhesiveness. Moreover, the photoresist should be easily developable in a readily available developing solution, such as 2.38% aqueous tetramethylammonium hydroxide (TMAH) solution. However, it is very difficult to synthesize a photoresist polymer, especially DUV photoresist, which meets all of these desired characteristics. For example, a polymer having a polyacrylate polymer backbone are readily available, but it has a poor etching resistance and is difficult to develop. In order to increase its etching resistance, several groups have added an alicyclic unit to the polymer backbone. However, photoresist copolymers comprising entirely of an alicyclic polymer backbone is difficult to form.

To solve some of the problems described above, Bell Research Center developed a polymer having the following chemical formula:

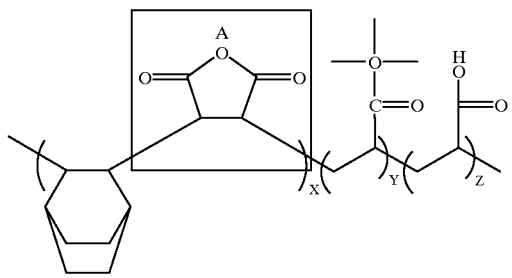

where the polymer backbone is substituted with a norbornene, an acrylate and a maleic anhydride unit. Unfortunately, even in the unexposed regions, the maleic anhydride moiety ('A' portion) dissolves readily in 2.38 wt % aqueous TMAH solution. Therefore, in order to inhibit the dissolution of the polymer in the unexposed section, the ratio of 'Y' portion having tert-butyl substituent must be increased, but this increase results in a relative decrease in the 'Z' portion, which is responsible for the adhesiveness of the photoresist polymer. This decrease in the relative amount of the 'Z' portion may result in separation of the photoresist from the substrate during a pattern formation.

In order to solve this problem, cholesterol type dissolution inhibitors have been added to the polymer to form a two-component system. However, since the amount of the dissolution inhibitor is very high [about 30% (w/w) of the resin], reproducibility is low and the production cost is high, thereby making the system unsuitable as a PR.

Therefore, there is a need for a photoresist polymer which provides an excellent etching properties, adhesiveness, ease of development, and good pattern formation.

SUMMARY OF THE INVENTION

An object of the present invention is to provide PR polymers having excellent etching resistance, adhesiveness and photosensitivity, and a process for preparing the same.

Specifically, the present invention provides novel PR monomers, in particular, bis(norbornene carboxylate) and bis(norbornene dicarboxylate) compounds, which comprise an acetal protecting group and a process for preparing the same.

Another object of the present invention is to provide photoresist compositions comprising the PR polymers described above, and a process for preparing the same.

Still another object of the present invention is to provide a semiconductor device produced by using the PR composition.

DETAILED DESCRIPTION OF THE INVENTION

The present invention provides photoresist monomers of the formula:

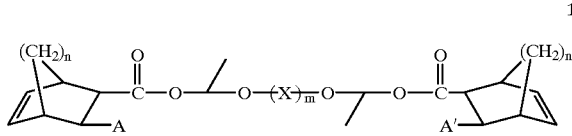

where A is hydrogen or —COOR$_1$; A' is hydrogen or —COOR$_2$; each of R$_1$ and R$_2$ is independently hydrogen or, substituted or non-substituted (C$_1$–C$_{10}$) linear of branched alkyl, cycloalkyl, alkoxyalkyl or cycloalkoxyalkyl; X is substituted or non-substituted (C$_1$–C$_{10}$) linear of branched alkyl, cycloalkyl, alkoxyalkyl or cycloalkoxyalkyl; m is an integer from 1 to 8; and n is an integer from 1 to 3. In the present invention, the compound of formula 1 is named using the following nomenclature: the bis(norbornene carboxylate) group is named first as bis(norbornene carboxylyl) followed by the group containing —O—(X)$_m$—O— as a dihydroxy group which is followed by the name diethyl ether. For example, a compound of formula 1 where A=H, m=1, n=1 and X=propyl would be called bis(5-norbornene-2-carboxylyl)-1,3-propanediol diethyl ether.

Thus, the compound of Formula 1 encompasses bis(norbornene carboxylate) of formula 1a and bis(norbornene dicarboxylate) of formula 1b:

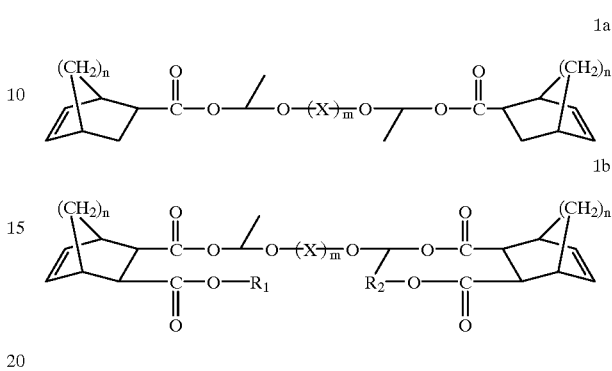

Preferably, R$_1$ and R$_2$ are selected from the group consisting of hydrogen, methyl, ethyl and tert-butyl. More preferably, R$_1$ and R$_2$ are identical.

The following are particularly preferred compounds of formula 1:

bis(5-norbornene-2-carboxylyl)-1,4-butanediol diethyl ether (2a);

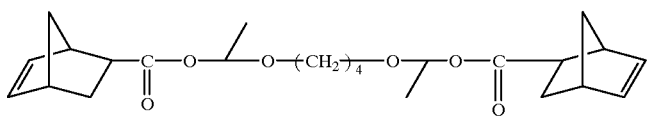

bis(5-norbornene-2,3-dicarboxylyl-1,4-butanediol diethyl ether (2b);

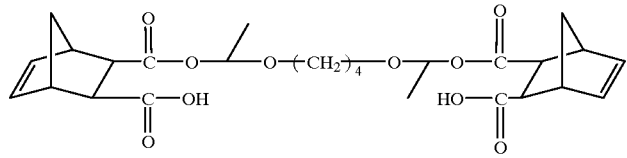

bis(5-norbornene-2-carboxylyl)-1,3-propanediol diethyl ether (3a);

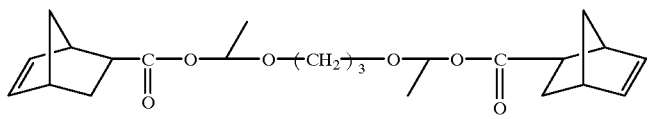

bis(5-norbornene-2,3-dicarboxylyl)-1,3-propanediol diethyl ether (3b);

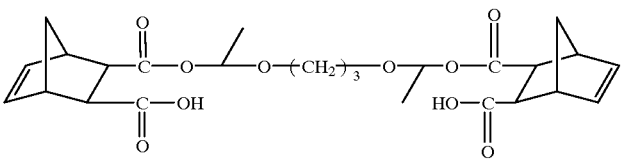

bis(5-norbornene-2-carboxylyl)-1,4-cyclohexane dimethanol diethyl ether (4a);

-continued

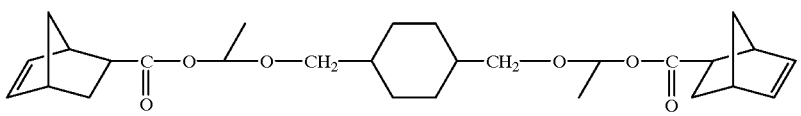

bis(5-norbornene-2,3-dicarboxylyl)-1,4-cyclohexane dimethanol diethyl ether (4b);

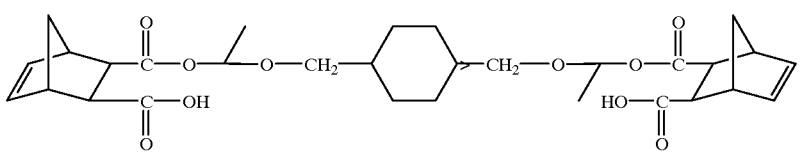

The compound of formula 1 can be prepared by reacting a compound of Formula 5:

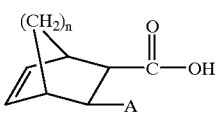

with a compound of Formula 6:

preferably in an organic solvent, in the presence of an acid catalyst, where A, X, m and n are those defined above. The reaction temperature is typically in the range of from about 10° C. to about 50° C. And the reaction time is generally from about 8 to about 12 hours. After the reaction, removal of the organic solvent typically affords the desired compound of formula 1.

While any non-protic organic solvent can be used in the preparation of compound of formula 1, typically tetrahydrofuran (THF), dimethylformamide, dioxane, benzene, toluene or xylene are used. In addition, it is within the knowledge of one skilled in the art of organic chemistry in selecting an appropriate acid catalyst for the above described method. Such acid catalyst includes any organic and inorganic acids. A preferred acid catalyst includes para-toluenesulfonic acid.

The compound of formula 5 is preferable selected from the group consisting of 5-norbornene-2-carboxylic acid and 5-norbornene-2,3-dicarboxylic acid. And preferably, a compound of formula 6 is selected from a group consisting of 1,4-butanediol divinyl ether, 1,3-propanediol divinyl ether and 1,4-cyclohexane dimethanol divinyl ether.

The present invention also provides photoresist copolymer comprising a compound of formula 1. As used herein, the term "photoresist copolymer comprising a compound" of formula 1 means a photoresist copolymer which is derived from polymerizing the compound of formula 1.

The photoresist copolymer of the present invention can also include a second monomer which is represented by a compound of the formula:

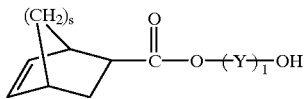

where Y is substituted or non-substituted ($C_1$–$C_{10}$) linear or branched alkyl, cycloalkyl, alkoxyalkyl or cycloalkoxyalkyl; 1 is an integer from 1 to 8, and s is an integer from 1 to 3. Preferably, the second monomer is selected from the group consisting of 2-hydroxyethyl5-norbornene-2-carboxylate or 3-hydroxypropyl 5-norbornene-2-carboxylate.

In addition, the photoresist copolymer of the present invention can also include a third monomer is selected from the group consisting of a compound of the formula:

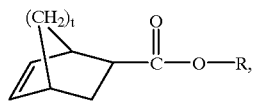

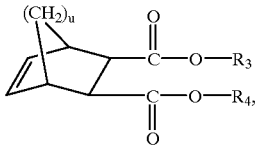

where each of R, $R_3$ and $R_4$ is independently hydrogen or substituted or non-substituted ($C_1$–$C_{10}$) linear or branched alkyl, cycloalkyl, alkoxyalkyl or cycloalkoxyalkyl; and each of t and u is independently an integer from 1 to 3. Preferably, a compound of formula 8 is tert-butyl-5-norbornene-2-carboxylate or 5-norbornene-2-carboxylic acid. And a preferred compound of formula 9 is 5-norbornene-2,3-dicarboxylic acid.

The photoresist copolymer of the present invention can also include maleic anhydride as a fourth monomer.

Preferably, the molecular weight of the PR copolymer of the present invention is in the range of from about 3000 to about 100,000.

Particularly preferred photoresist copolymers of the present invention includes: poly[bis(5-norbornene-2-carboxylyl)-1,4-butanediol diethyl ether/2-hydroxyethyl-5norbornene-2-carboxylate/tert-butyl-5-norbornene-2-carboxylate/5-norbornene-2-carboxylic acid/maleic anhydride](10):

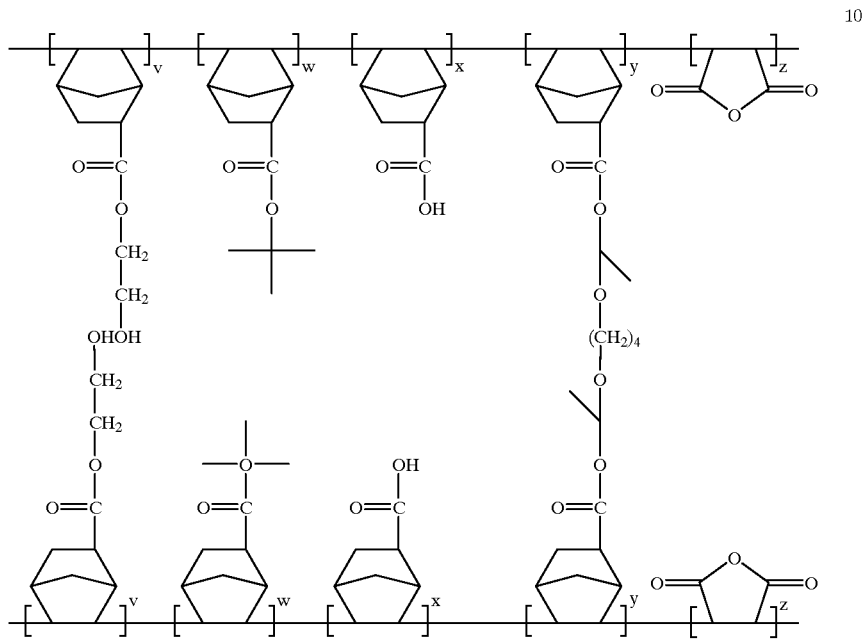
Poly[bis(5-norbornene-2-carboxylyl)-1,3-propandioldiethylether/2-hydroxyethyl-5-norbornene-2-carboxylate/tert-butyl-5-norbornene-2-carboxylate/5-norbornene-2-carboxylic acid/maleic anhydride] (11):
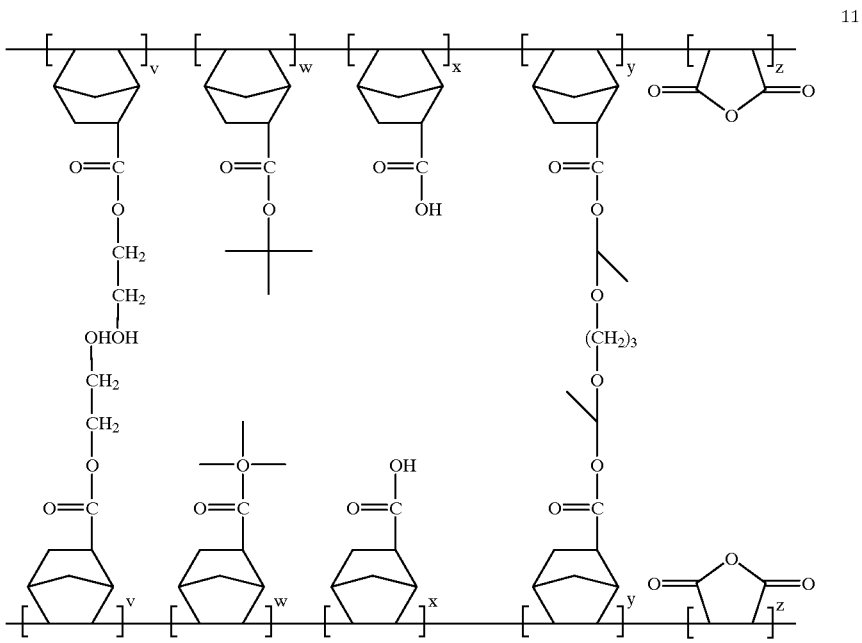

Poly[bis(5-norbornene-2-carboxylyl)-1,4-cyclohexane dimethanol diethylether/2-hydroxyethyl-5-norbornene-2-carboxylate/tert-butyl-5-norbornene-2-carboxylate/5-norbornene-2-carboxlic acid/maleic anhydride] (12):
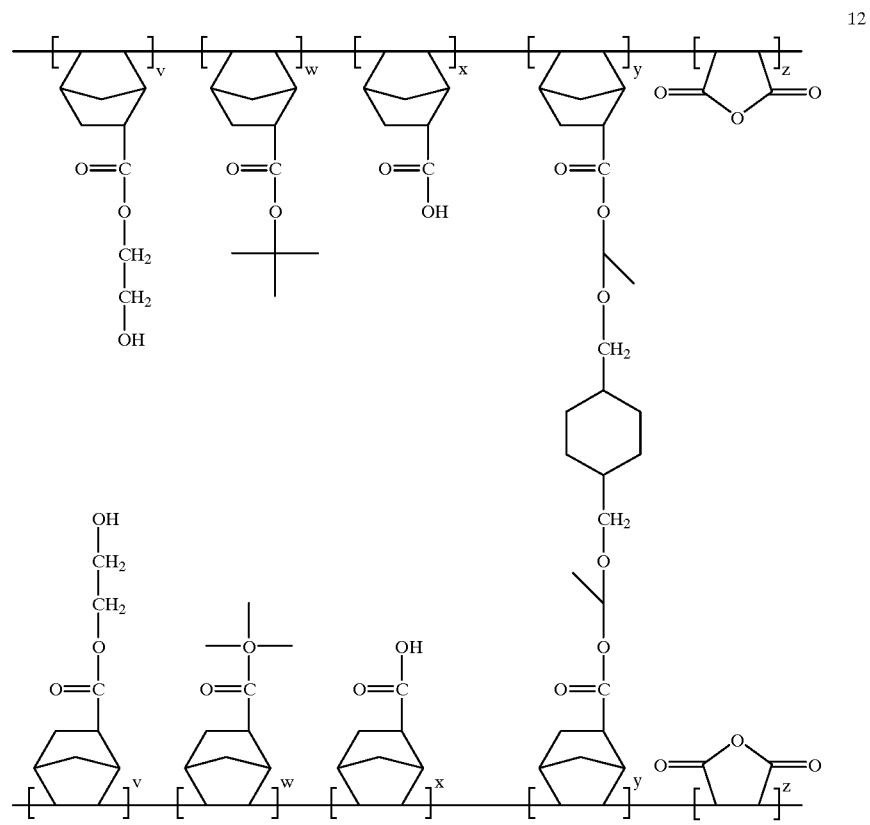
Poly[bis(5-norbornene-2,3-dicarboxylyl)-1,4-butanedioldiethyether/2-hydroxyethyl-5-norbornene-2-carboxylate/tert-butyl-5-norbornene-2-carboxylate/maleic anhydride] (13):
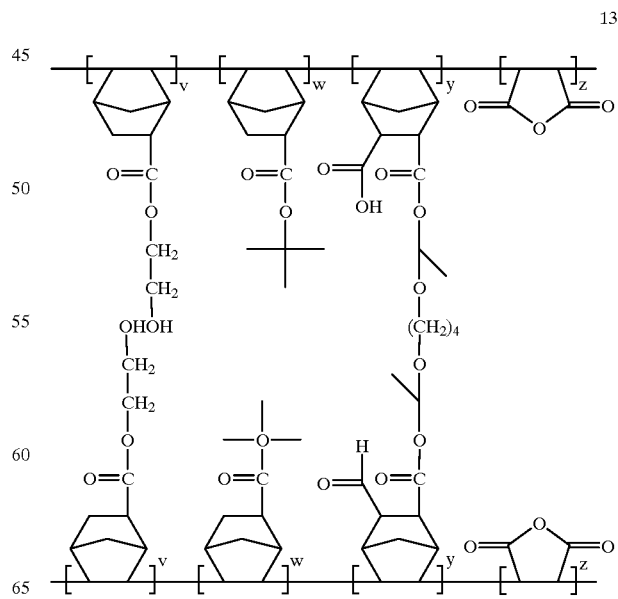

Poly[bis(5-norbornene-2,3-dicarboxylyl)-1,3-propanediol diethyl ether/2-hydroxyethyl-5-norbornene-2-carboxylate/tert-butyl-5-norbornene-2-carboxylate/5-norbornene-2-carboxylic acid/maleic anhydride ] (14):

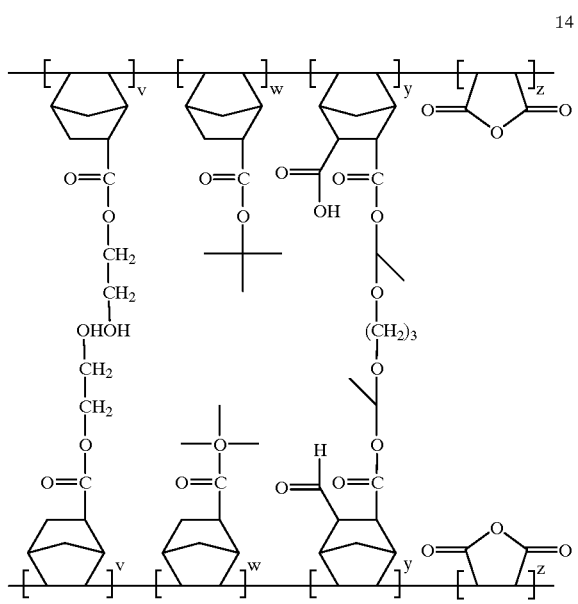

Poly[bis(5-norbornene-2,3-dicarboxylyl)-1,4-cyclohexane dimethanol diethyl ether/2-hydroxyethyl-5-norbornene-2-carboxylate/tert-butyl-5-norbornene-2-carboxylate/5-norbornene-2-carboxylic acid/maleic anhydride] (15):

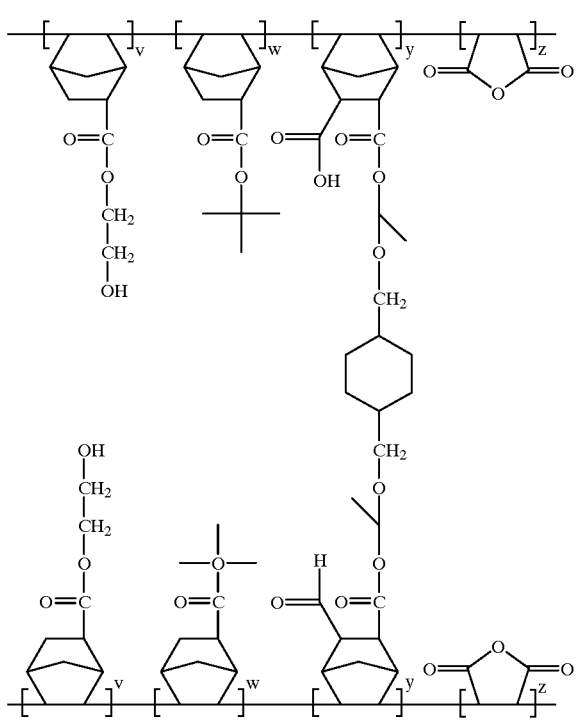

For the compounds of Formulas 10–15, v, w, x, y and z represents the relative amounts of each monomer, wherein the ratio of v:w:x:y:z=0~99 mol %:0~99 mol %:0~99 mol %:0.1~99 mol %:0~99 mol %.

The photoresist copolymer of the present invention can be prepared by radical polymerization of monomers with a typical radical polymerization initiator. For example, a typical polymerization reaction includes (a) admixing, preferably in an organic solvent, (i) a compound of Formula 1 (the first monomer), (ii) a compound of Formula 7 (the second monomer), optionally (iii) more than one compound of Formula 8 and/or 9 (the third monomer), and (iv) maleic anhydride (the fourth monomer); (b) adding a polymerization initiator to the admixture; and (c) polymerizing the admixture obtained from (b) in an inert atmosphere, preferably in a nitrogen or argon atmosphere.

Alternatively, the photoresist copolymer in the present invention can be prepared by reacting the photoresist copolymer—obtained from polymerizing a compound of Formula 7, more than one compound of Formula 8 and/or 9, and maleic anhydride—with a compound of Formula 6 in the presence of an acid catalyst.

In the present invention, polymerization is carried out by either a bulk polymerization or a solution polymerization. A preferred polymerization solvent is selected from the group consisting of cyclohexanone, tetrahydrofuran, dimethylformamide, dimethylsulfoxide, dioxane, methyl ethyl ketone, benzene, toluene and xylene. The polymerization initiator is preferably selected from the conventional radical polymerization initiators, such as benzoylperoxide, 2,2'-azobisisobutyronitrile (AIBN), acetylperoxide, laurylperoxide, tert-butylperacetate, tert-butylhydroperoxide and di-tert-butylperoxide.

As shown above, the photoresist copolymer of the present invention is partially cross-linked. In an exposed region, both the acid labile protecting group and the acetal group are deprotected by the acid that is generated in photolithography. This deprotection results in a large difference in the solubility rate between in the exposed region and the unexposed region, and as a result, decreases top-loss and enhances profile.

The present invention also provides a PR composition comprising the PR copolymer described above, an organic solvent, and a photoacid generator. Preferred photoacid generators include sulfide or onium type compounds. A suitable photoacid generator may be one or more compounds selected from the group consisting of diphenyl iodide hexafluorphosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluoroantimonate, triphenylsulfonium triflate and dibutylnaphthylsulfonium triflate. The photoacid generator is typically used in an amount of from about 0.1% by weight to about 10% by weight of the photoresist copolymer.

Useful organic solvents for the photoresist composition include methyl 3-methoxypropionate, ethyl 3-ethoxypriopionate, propylene glycol methyl ether acetate, cyclohexanone, 2-heptanone, and (2-methoxy)ethyl acetate. Preferably, the amount of organic solvent present in the photoresist composition of the present invention is in the range of from about 200% by weight to about 1000% by weight of the PR copolymer.

The PR composition is typically prepared by dissolving the photoresist copolymer of the present invention in an organic solvent in the amount ranging from about 10% by weight to about 30% by weight of the solvent, blending the photoacid generator with the photoresist copolymer in the amount ranging from about 0.1% by weight to about 10% by weight of the copolymer and then filtering the resulting mixture through a hyperfine filter.

The PR composition of the present invention has an excellent etching resistance, adhesiveness and heat resistance. Also, it has an excellent resolution and profile because it is partially cross-linked. Moreover, the PR composition of the present invention reduces top-loss of the photoresist, and therefor is very useful as an ArF photosensitive film.

The present invention also provides the method for forming the PR pattern comprising the steps of: (a) coating the above described photoresist composition on a substrate of semiconductor element to form a photoresist film; (b) exposing the photoresist film to light using a light source; and (c) developing the photoresist film. Optionally, the photoresist film can be heated (i.e., baked), preferably to temperature in the range of from about 70° C. to about 200° C., before and/or after the step (b).

Exemplary light sources which are useful for forming the PR pattern include ArF (193 nm), KrF (248 nm), VUV (157 nm), EUV, E-beam, X-ray and ion beam. Preferably, the irradiation energy is in the range of from about 1 mJ/cm$^2$ to about 100 mJ/cm$^2$.

In one particular example, the photoresist pattern formation process of the present invention comprises the steps of: i) forming a thin-film of PR composition by spin coating the photoresist composition of the present invention on a silicon wafer; ii) soft baking the silicon wafer in an oven or on a hot plate at temperature in the range of from about 80° C. to about 150° C. for 1 to 5 minutes; iii) exposing the silicon wafer to light using an ArF exposer or excimer laser; and iv) baking the exposed wafer at temperature in the range of from about 100° C. to about 200° C. The exposed silicon wafer is developed by immersing it in a 2.38 wt % TMAH solution for 90 seconds to get hyperfine resist image.

The present invention also provides a semiconductor device, which is manufactured using the photoresist composition described above.

Additional objects, advantages, and novel features of this invention will become apparent to those skilled in the art upon examination of the following examples thereof, which are not intended to be limiting.

PREPARATION OF NOVEL PHOTORESIST MONOMERS

Preparation Example 1
Synthesis of 2-hydroxyethyl-5-norbornene-2-carboxylate About 66 g of cyclopentadiene is dissolved in about 500 g of tetrahydrofuran (THF). To the resulting mixture was added 130 g of 2-hydroxyethyl acrylate, and the reaction mixture was stirred at −30° C. for 10 hours. The solvent was removed by distillation through a rotary distiller. The title compound was obtained by distillation under reduced pressure (yield: 85%).

Preparation Example 2
Synthesis of tert-butyl-5-norbornene-2-carboxylate

The procedure of Example 1 was repeated except that 128 g of tert-butyl acrylate was used instead of 130 g of 2-hydroxyethyl acrylate (yield: 90%).

Preparation Example 3
Synthesis of 5-norbornene-2-carboxylic Acid

The procedure of Example 1 was repeated except that 72 g of acrylic acid was used instead of 130 g of 2-hydroxyethyl acrylate (yield 90%).

Invention Example 1
Synthesis of bis(5-norbornene-2-carboxylyl)-1,4-butanediol Diethyl Ether 13.8 g of 5-norbornene-2-carboxylic acid from Preparation Example 3 was dissolved in 100 g of THF solution. To the resulting solution was added 0.1 g of para-toluenesulfonic acid and 7.1 g of 1,4-butanediol divinyl ether. The reaction mixture was stirred at temperature in the range of from about 10° C. to about 15° C. for about 10 hours. After which the solvent, THF, was removed by a rotary distiller, and the title compound represented by Chemical Formula 2 was obtained by distillation under reduced pressure (yield 88%).

Invention Example 2
Synthesis of bis(5-norbornene-2-carboxylyl)-1,3-propanediol Diethyl Ether The procedure of Invention Example 1 was repeated except that 6.4 g of 1,3-propanediol divinyl ether was used instead of 7.1 g of 1,4-butanediol divinyl ether to obtain the title compound represented by Chemical Formula 3 (yield 89%).

Invention Example 3
Synthesis of bis(5-norbornene-2-carboxylyl)-1,4-cyclohexanedimethanol Diethyl Ether The procedure of Invention Example 1 was repeated except that 0.12 g of para-toluenesulfonic acid was used instead of 0.1 g of para-toluenesulfonic acid, and 9.8 g of 1,4-cyclohexanedimethanol divinyl ether was used instead of 7.1 g of 1,4-butanediol divinyl ether obtain the title compound represented by Chemical Formula 4 (yield 86%).

PREPARATION OF PHOTORESIST POLYMERS

Invention Example 4
Synthesis of Poly[bis(5-norbornene-2-carboxylyl)-1,4-butanediol diethyl ether/2-hydroxyethyl-5-norbornene-2-carboxylylate/tert-butyl-5-norbornene-2-carboxylate/5-norbornene-2-carboxylic acid/maleic anhydride]

To a solvent such as THF, benzene or toluene was added 0.1 mole of bis(5-norbornene-2-carboxylyl)-1,4-butanediol diethyl ether, 0.2 mole of 2-hydroxyethyl-5-norbornene-2-carboxylate, 0.65 mole of tert-butyl-5-norbornene-2-carboxylate, 0.05 mole of 5-norbornene-2-carboxylic acid and 1 mole of maleic anhydride. Then, 0.6 g of polymerization initiator, e.g., AIBN, was added to the resultant solution and the reaction was carried out in a Nitrogen or an Argon atmosphere at approximately 70° C. for about 12 hours. The resulting resin was precipitated in ethyl ether or hexane, filtered, and dried under reduced pressure to obtain the partially cross-linked polymer represented by Chemical Formula 10.

Invention Example 5
Synthesis of ploy[bis(5-norbornene-2-carboxylyl)-1,3-propanediol diethyl ether/2-hydroxyethyl-5-norbornene-2-carboxylate/tert-butyl-5-norbornene-2-carboxylate/5-norbornene-2-carboxylic acid/maleic Anhydride]

To benzene solvent was added 0.1 mole of bis(5-norbornene-2-carboxylyl)-1,3-propanediol diethyl ether, 0.2 mole of 2-hydroxyethyl-5-norbornene-2-carboxylate, 0.65 mole of tert-butyl-5-norbornene-2-carboxylate, 0.05 mole of 5-norbornene-2-carboxylic acid and 1 mole of maleic anhydride. Then, 0.6 g of polymerization initiator, e.g., AIBN, was added to the solution, and the reaction was carried out in a Nitrogen or an Argon atmosphere at temperature of about 70° C. for about 12 hours. The resulting resin was precipitated in ethylether or hexane, and filtered under reduced pressure to obtain the partially cross-linked polymer represented by Chemical Formula 11.

Invention Example 6
Synthesis of poly[bis(5-norbornene-2-carboxylyl)-1,4-cyclohexane dimethanol diethyl ether/2-hydroxyethyl-5-norbornene-2-carboxylate/tert-butyl-5-norbornene-2-carboxylate/5-norbornene-2-carboxylic acid/maleic Anhydride]

To benzene solvent was added 0.1 mole of bis(5-norbornene-2-carboxylyl)-1,4-cyclohexane dimethanol diethyl ether, 0.2 mole of 2-hydroxyethyl-5-norbornene-2-carboxylate, 0.65 mole of tert-butyl-5-norbornene-2-carboxylate, 0.05 mole of 5-norbornene-2-carboxylic acid and 1 mole of maleic anhydride. Then, 0.6 g of polymerization initiator, AIBN, was added to the solution, and the reaction was carried out in a Nitrogen or an Argon atmosphere at temperature of about 70° C. for about 12 hours. The resulting resin was precipitated in ethylether or hexane, and filtered under reduced pressure to obtain the partially cross-linked polymer represented by Chemical Formula 12.

The copolymers obtained from the Invention Examples 4 through 6 can also be prepared using the following Invention Examples 7 through 9.

Invention Examples 7–9

The mixture of monomers that were used in the Invention Examples 4–6 for copolymerization, excluding the monomers bis(5-norbornene-2-carboxylyl)-1,4butanediol diethyl ether, bis(5-norbornene-2-carboxylyl)-1,3-propanediol diethyl ether and bis(5-norbornene-2-carboxylyl)-1,4-cyclohexane dimethanol diethyl ether, respectively, were polymerized and the copolymers obtained therefrom were dissolved in tetrahydrofuran. Then, 0.1 mole of 1,4-butanediol divinyl ether, 1,3-propanediol divinyl ether or 1,4-cyclohexane dimethanol divinyl ether, respectively, and an acid catalyst were added to the resulting solution. The reaction mixture was stirred for 10 hours, and the resulting mixture diluted with dimethylether to obtain the title partially cross-linked polymers of the Invention Examples 4–6, respectively.

Invention Example 10
Synthesis of poly[bis(5-norbornene-2,3-dicarboxylyl)/1,4-butanediol diethyl ether/2-hydroxyethyl-5-norbornene-2-carboxylate/tert-butyl-5-norbornene-2-carboxylate/maleic Anhydride]

To THF solvent was added 0.2 mole of 2-hydroxyethyl-5-norbornene-2-carboxylate, 0.75 mole of tert-butyl-5-norbornene-2-carboxylate, 0.05 mole of 5-norbornene-2,3-dicarboxylic acid and 1 mole of maleic anhydride. Then, 0.6 g AIBN was added to the solution, and the reaction was carried out in a Nitrogen or an Argon atmosphere at about 70° C. for 12 hours. After which the resulting resin was precipitated in ethylether or hexane, filtered, and dried under reduced pressure to obtain a polymer. 10 g of the polymer obtained was then dissolved in 100 mL of THF and was reacted again with 0.01 mol of 1,4-butanediol divinyl ether for 10 hours in the presence of para-toluenesulfonic acid (0.05 mole) to obtain the partially cross-linked compound represented by Chemical Formula 13.

Invention Example 11
Synthesis of ploy[bis(5-norbornene-2,3-dicarboxylyl)-1,3-propanediol diethyl ether/2-hydroxyethyl-5-norbornene-2-carboxylate/tert-butyl-5-norbornene-2-carboxylate/5-norbornene-2-carboxylic acid/maleic Anhydride To THF solvent was added 0.2 mole of 2-hydroxyethyl-5-norbornene-2-carboxylate, 0.75 mole of tert-butyl-5-norbornene-2-carboxylate, 0.05 mole of 5-norbornene-2,3-dicarboxylic acid and 1 mole of maleic anhydride. Then, 0.6 g of AIBN was added to the solution, and the reaction was carried out in a Nitrogen or an Argon atmosphere at about 70° C. for 12 hours. After which the resulting resin was precipitated in ethylether or hexane, filtered, and dried under reduced pressure to obtain a polymer. About 10 g of the polymer obtained was then dissolved in 100 mL of THF and was reacted again with 0.01 mol of 1,3-propanediol divinyl ether for 10 hours in presence of para-toluenesulfonic acid (0.05 mole), to obtain the partially cross-linked compound represented by Chemical Formula 14.

Invention Example 12
Synthesis of poly[bis(5-norbornene-2,3-dicarboxylyl)-1,4-cyclohexane dimethanol diethyl ether/2-hydroxyethyl-5-norbornene-2-carboxylate/tert-butyl-5-norbornene-2-carboxylate/5-norbornene-2-carboxylic acid/maleic Anhydride To THF solvent was added 0.2 mole of 2-hydroxyethyl-5-norbornene-2-carboxylate, 0.75 mole of tert-butyl-5-norbornene-2-carboxylate, 0.05 mole of 5-norbornene-2,3-dicarboxylic acid and 1 mole of maleic anhydride. Then, 0.6 g AIBN was added into the solution, and the reaction was carried out in a Nitrogen or an Argon atmosphere at about 70° C. for 12 hours. After which the resulting resin was precipitated in ethylether or hexane, filtered, and dried under reduced pressure to obtain a polymer. About 10 g of the polymer obtained was then dissolved in 100 mL of THF and was reacted again with 0.01 mol of 1,4-cyclohexane dimethanol divinyl ether for 10 hours in the presence of para-toluenesulfonic acid (0.05 mole), to obtain the partially cross-linked compound represented by Chemical Formula 15.

PREPARATION OF PHOTORESIST COMPOSITIONS, AND FORMATION OF A PHOTORESIST PATTERN BY USING THE SAME

Invention Example 13

10 g of the polymer which was prepared from the Invention Example 4 was dissolved in 60 g of propyleneglycol methyletheracetate. To this solution was added 1.12 g of triphenylsulfonium triflate. The resulting solution was stirred and filtered through 0.1 μm filter to prepare a PR composition.

The photoresist composition thus prepared was spin-coated on a silicon wafer, and soft-baked at 80° C. to 150° C. for 1 to 5 minutes. After baking, the photoresist was exposed to light by using an ArF laser exposer, and then post-baked at 100° C. to 200 ° C. The resulting silicon wager was developed in 2.38 wt % aqueous TMAH solution for 90 seconds to obtain a 0.13 μm L/S pattern on the resist having the thickness of approximately 0.5 μm.

Invention Example 14

The procedure of Invention Example 13 was repeated except that the copolymer obtained from Invention Example 5 was used instead of the copolymer obtained from Invention Example 4 to prepare a PR composition. In this manner, a 0.13 μm L/S pattern was created on the resist having the thickness of approximately 0.5 μm.

Invention Example 15

The procedure of Invention Example 13 was repeated except that the copolymer obtained from Invention Example 6 was used instead of the copolymer obtained from Invention Example 4 to prepare a PR composition. In this manner, a 0.13 μm L/S pattern was created on the resist having the thickness of approximately 0.5 μm.

Invention Example 16

The procedure of Invention Example 13 was repeated except that the copolymer obtained from Invention Example 10 was used instead of the copolymer obtained from Invention Example 4 to prepare a PR composition. In this manner, a 0.13 μm L/S pattern was created on the resist having the thickness of approximately 0.5 μm.

Invention Example 17

The procedure of Invention Example 13 was repeated except that the copolymer obtained from Invention Example 11 was used instead of the copolymer obtained from Invention Example 4 to prepare a PR composition. In this manner, a 0.13 μm L/S pattern was created on the resist having the thickness of approximately 0.5 μm.

Invention Example 18

The procedure of Invention Example 13 was repeated except that the copolymer obtained from Invention Example 11 was used instead of the copolymer obtained from Invention Example 4 to prepare a PR composition. In this manner, a 0.13 μm L/S pattern was created on the resist having the thickness of approximately 0.5 μm.

The PR composition of the present invention comprising the partially cross-linked copolymers reduces top-loss of the resist during development, provides an excellent profile and resolution, and allows creation of a 0.13 μm L/S pattern on the resist having the thickness of approximately 0.5 μm. In addition, by using the partially cross-linked photoresist polymer of the present invention, a high quality PR film having an excellent resolution, profile and reduced top-loss can be obtained.

What is claimed is:

1. A photoresist monomer of the formula:

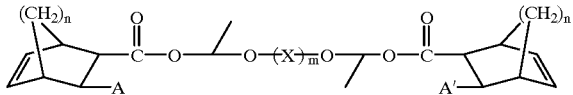

wherein A is hydrogen or a moiety of the formula —$COOR_1$; A' is hydrogen or a moiety of the formula —$COOR_2$; each of $R_1$ and $R_2$ is independently hydrogen or, substituted or non-substituted ($C_1$–$C_{10}$) linear of branched alkyl, cycloalkyl, alkoxyalkyl or cycloalkoxyalkyl; X is substituted or non-substituted ($C_1$–$C_{10}$) linear of branched alkyl, cycloalkyl, alkoxyalkyl or cycloalkoxyalkyl; m is an integer from 1 to 8, and n is an integer from 1 to 3.

2. The photoresist monomer according to claim 1, wherein $R_1$ and $R_2$ are selected from the group consisting of hydrogen, methyl, ethyl and tert-butyl.

3. The photoresist monomer according to claim 1, which is selected from the group consisting of bis(5-norbornene-2-carboxylyl)-1,4-butanediol diethyl ether; bis(5-norbornene-2-carboxylyl)-1,3-propanediol diethyl ether; bis(5-norbornene-2-carboxylyl)-1,4-cyclohexane dimethanol diethyl ether; bis(5-norbornene-2,3-dicarboxylyl)-1,4-butanediol diethyl ether; bis(5-norbornene-2,3-dicarboxylyl)-1,3-propanediol diethyl ether; and bis(5-norbornene-2,3-dicarboxylyl)-1,4-cyclohexane dimethanol diethyl ether.

4. A process for preparing the photoresist monomer of claim 1 comprising the steps of:
(a) dissolving a carboxylic acid of formula 5 in an organic solvent

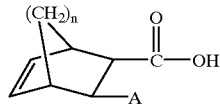

(b) reacting said carboxylic acid of formula 5 with a vinyl ether of formula 6 in the presence of an acid catalyst

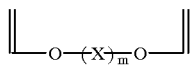

to produce said photoresist monomer of claim 1; and
(c) recovering said photoresist monomer of claim 1, wherein A is hydrogen or a moiety of the formula —$COOR_1$; $R_1$ is hydrogen or substituted or non-substituted ($C_1$–$C_{10}$) linear or branched alkyl, cycloalkyl, alkoxyalkyl or cycloalkoxyalkyl; X is substituted or non-substituted ($C_1$–$C_{10}$) linear or branched alkyl, cycloalkyl, alkoxyalkyl or cycloalkoxyalkyl; m is an integer from 1 to 8, and n is an integer from 1 to 3.

5. The process according to claim 4, wherein said organic solvent is selected from the group consisting of tetrahydrofuran (THF), dimethylformamide, dimethylsulfoxide, dioxane, benzene, toluene and xylene.

6. The process according to claim 4, wherein said catalyst is para-toluenesulfonic acid.

7. The process according to claim 4, wherein said carboxylic acid of formula 5 is 5-norbornene-2-carboxylic acid or 5-norbornene-2,3-dicarboxylic acid; and said vinyl ether of formula 6 is selected from the group consisting of 1,4-butanediol divinyl ether, 1,3-propanediol divinyl ether and 1,4-cyclohexane dimethanol divinyl ether.

8. A photoresist copolymer derived from a photoresist monomer of formula 1:

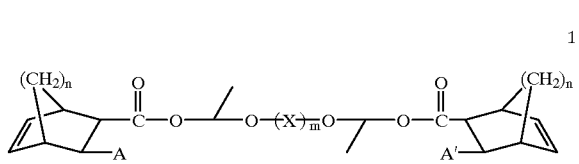

wherein A is hydrogen or a moiety of the formula —COOR$_1$; A' is hydrogen or a moiety of the formula —COOR$_2$; each of R$_1$ and R$_2$ is independently hydrogen or, substituted or non-substituted (C$_1$–C$_{10}$) linear of branched alkyl, cycloalkyl, alkoxyalkyl or cycloalkoxyalkyl; X is substituted or non-substituted (C$_1$–C$_{10}$) linear of branched alkyl, cycloalkyl, alkoxyalkyl or cycloalkoxyalkyl; m is an integer from 1 to 8, and n is an integer from 1 to 3.

9. The photoresist copolymer according to claim 8, further comprising a second monomer of the formula 7:

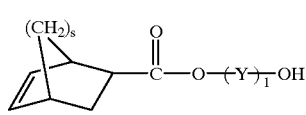

wherein Y is substituted or non-substituted (C$_1$–C$_{10}$) linear or branched alkyl, cycloalkyl, alkoxyalkyl or cycloalkoxyalkyl; l is an integer from 1 to 8, and s is an integer from 1 to 3.

10. The photoresist copolymer according to claim 9, wherein said second monomer of formula 7 is 2-hydroxyethyl-5-norbornene-2-carboxylate or 3-hydroxypropyl-5-norbornene-2-carboxylate.

11. The photoresist copolymer according to claim 8 further comprising a third monomer, wherein said third monomer is selected from the group consisting of a compound of the formula:

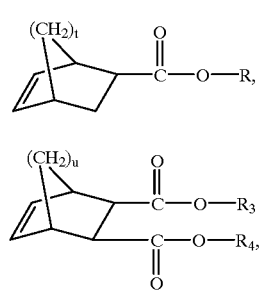

wherein each of R, R$_3$ and R$_4$ is independently hydrogen or substituted or non-substituted (C$_1$–C$_{10}$) linear or branched alkyl, cycloalkyl, alkoxyalkyl or cycloalkoxyalkyl; and each of t and u is independently an integer from 1 to 3.

12. The photoresist copolymer according to claim 11, wherein said third monomer is selected from the group consisting of tert-butyl-5-norbornene-2-carboxylate or 5-norbornene-2-carboxylic acid, 5-norbornene-2,3-dicarboxylic acid, and mixtures thereof.

13. The photoresist copolymer according to claim 11 further comprising maleic anhydride as a fourth comonomer.

14. The photoresist copolymer according to claim 8, of wherein the molecular weight of said photoresist copolymer is in the range of from about 3000 to about 100,000.

15. The photoresist copolymer according to claim 8, which is selected from the group consisting of:

poly[bis(5-norbornene-2-carboxylyl)-1,4-butanediol diethyl ether/2-hydroxyethyl-5-norbornene-2-carboxylate/tert-butyl-5-norbornene-2-carboxylate/5-norbornene-2-carboxylic acid/maleic anhydride];

Poly[bis(5-norbornene-2-carboxylyl)-1,3-propandioldiethylether/2-hydroxyethyl-5-norbornene-2-carboxylate/tert-butyl-5-norbornene-2-carboxylate/5-norbornene-2-carboxylic acid/maleic anhydride];

Poly[bis(5-norbornene-2-carboxylyl)-1,4-cyclohexane dimethanol diethylether/2-hydroxyethyl-5-norbornene-2-carboxylate/tert-butyl-5-norbornene-2-carboxylate/5-norbornene-2-carboxlic acid/maleic anhydride];

Poly[bis(5-norbornene-2,3-dicarboxylyl)-1,4-butanedioldiethyether/2-hydroxyethyl-5-norbornene-2-carboxylate/tert-butyl-5-norbornene-2-carboxylate/maleic anhydride];

Poly[bis(5-norbornene-2,3-dicarboxylyl)-1,3-propanediol diethyl ether/2-hydroxyethyl-5-norbornene-2-carboxylate/tert-butyl-5-norbornene-2-carboxylate/5-norbornene-2-carboxylic acid/maleic anhydride]; and Poly[bis(5-norbornene-2,3-dicarboxylyl)-1,4-cyclohexane dimethanol diethyl ether/2-hydroxyethyl-5-norbornene-2-carboxylate/tert-butyl-5-norbornene-2-carboxylate/5-norbornene-2-carboxylic acid/maleic anhydride].

16. A process for preparing a photoresist copolymer, which comprises the steps of:

(a) admixing
(i) a first monomer of the compound formula 1:

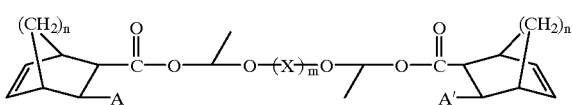

(ii) a second monomer of the formula 7:

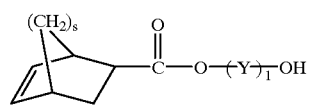

optionally (iii) a third monomer comprising more than one compound selected from the group consisting of a compound of the formula:

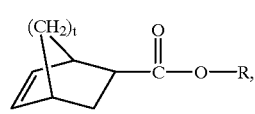

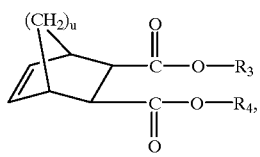

(iv) maleic anhydride;
(b) adding polymerization initiator thereto; and
(c) polymerizing said admixture of step (b) in an inert atmosphere.
wherein A is hydrogen or a moiety of the formula —COOR$_1$; A' is hydrogen or a moiety of the formula —COOR$_2$; each of R, R$_1$, R$_2$, R$_3$ and R$_4$ is independently hydrogen or, substituted or non-substituted (C$_1$–C$_{10}$) linear of branched alkyl, cycloalkyl, alkoxyalkyl or cycloalkoxyalkyl; each of X and Y is independently substituted or non-substituted (C$_1$–C$_{10}$) linear of branched alkyl, cycloalkyl, alkoxyalkyl or cycloalkoxyalkyl; each of m and 1 is independently an integer from 1 to 8; and each of n, s, t and u is independently an integer from 1 to 3.

17. The process according to claim 16, wherein said admixture further comprises an organic solvent selected from the group consisting of cyclohexanone, tetrahydrofuran (THF), dimethylformamide, dimethylsulfoxide, dioxane, methyl ethyl ketone, benzene, toluene and xylene.

18. The process according to claim 16, wherein said polymerization initiator is selected from the group consisting of benzoyl peroxide, 2,2'-azobisisobutyronitrile (AIBN), acetyl peroxide, lauryl peroxide, tert-butyl peracetate, tert-butyl hydeperoxide and di-tert-buty peroxide.

19. A process for preparing a photoresist copolymer comprising the steps of:
(a) admixing
(i) more than one compound selected from the group consisting of a compound of the formula:

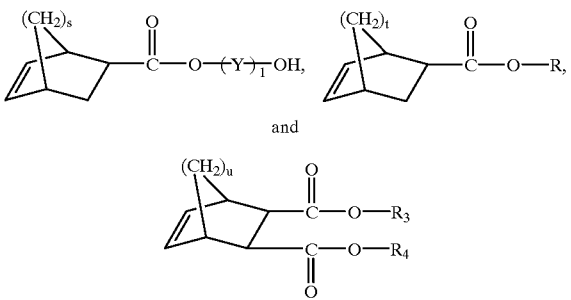

(ii) maleic anhydride; and
(iii) a polymerization initiator; in an inert atmosphere to produce a non-cross linked polymer; and
(b) reacting the non-cross linked polymer with a compound of the formula:

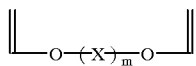

in the presence of an acid catalyst to produce said photoresist copolymer, wherein each of R, R$_3$ and R$_4$ is independently hydrogen or, substituted or non-substituted (C$_1$–C$_{10}$) linear of branched alkyl, cycloalkyl, alkoxyalkyl or cycloalkoxyalkyl; each of X and Y is independently substituted or non-substituted (C$_1$–C$_{10}$) linear of branched alkyl, cycloalkyl, alkoxyalkyl or cycloalkoxyalkyl; each of m and 1 is independently an integer from 1 to 8; and each of s, t and u is independently an integer from 1 to 3.

20. A photoresist composition comprising a photoresist copolymer of claim 8, an organic solvent and a photoacid generator.

21. The photoresist composition according to claim 20, wherein said photoacid generator is sulfide or onium type compound.

22. The photoresist composition according to claim 20, wherein the photoacid generator is a compound selected from the group consisting of diphenyl iodide hexafluorophosphate, diphenyl iodide hexafluoroarsenate, diphenyliodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophsphate, triphenylsulfonium hexafluoroarsenate, triphenylsulfonium hexafluoroantimonate, triphenylsulfonium triflate, dibutylnaphthylsulfonium triflate, and mixtures thereof.

23. The photoresist composition according to claim 20, wherein the amount of said photoacid generator is in the range of from about 1.0% by weight to about 10% by weight of the said photoresist copolymer.

24. The photoresist composition according to claim 20, wherein said organic solvent is selected from the group consisting of methyl 3-methoxypropionate, ethyl 3-ethoxypropionate, propylene glycol methyl ether acetate, cyclohexanone, 2-heptanone and (2-methoxy)ethyl acetate.

25. The photoresist composition according to claim 20, wherein the amount of said organic solvent is in the range of from about 200% by weight to about 1000% by weight of said photoresist copolymer.

26. A process for forming a photoresist pattern comprising the steps of (a) coating a photoresist composition of claim 20 on a substrate of semiconductor device to form a photoresist film; (b) exposing said photoresist film to light using a light source; and (c) developing said exposed photoresist film.

27. The process according to claim 26, wherein further comprises heating said photoresist film before and/or after said step (b).

28. The process according to claim 27, wherein said photoresist film is heated to temperature in the range of from about 70° C. to about 200° C.

29. The process according to claim 26, wherein said light source is ArF, KrF, VUV, EUV, E-beam, X-ray or ion-beam.

30. The process according to claim 26, wherein said photoresist film is carried irradiated with from about 0.1 mJ/cm$^2$ to about 100 mJ/cm$^2$ of light-exposure energy.

31. A semiconductor device manufactured by the process of claim 26.

* * * * *

UNITED STATES PATENT AND TRADEMARK OFFICE
CERTIFICATE OF CORRECTION

PATENT NO.   : 6,368,770 B1                                              Page 1 of 2
DATED        : April 9, 2002
INVENTOR(S)  : Min Ho Jung, Jae Chang Jung, Geun Su Lee and Ki Ho Baik It is certified that error appears in the above-identified patent and that said Letters Patent is hereby corrected as shown below:

Column 6,
Lines 29-30, the "2-hydroxyethyl5-norbornene-2-carboxylate" should read -- 2-hydroxyethyl 5-norbornene-2-carboxylate --.
Line 49, before "where each", please add -- and mixtures thereof; --.
Line 65, the "5norbornene-2-carboxylate" should read -- 5-norbornene-2-carboxylate --.

Column 10,
Lines 45-65, the chemical formula 13 should read --

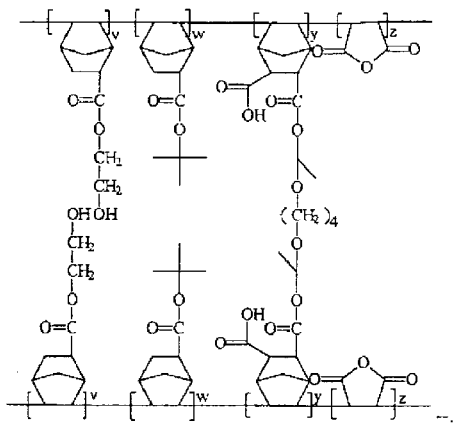

Column 11,
Lines 7-27, the chemical formula 14 should read --

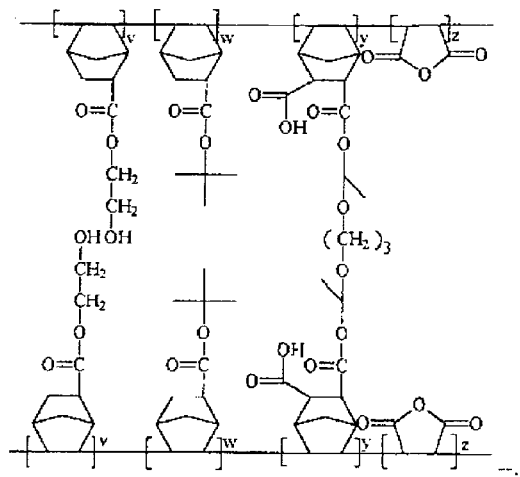

UNITED STATES PATENT AND TRADEMARK OFFICE
CERTIFICATE OF CORRECTION

PATENT NO. : 6,368,770 B1
DATED : April 9, 2002
INVENTOR(S) : Min Ho Jung, Jae Chang Jung, Geun Su Lee and Ki Ho Baik It is certified that error appears in the above-identified patent and that said Letters Patent is hereby corrected as shown below:

Column 11,
Lines 36-62, the chemical formula 15 should read --

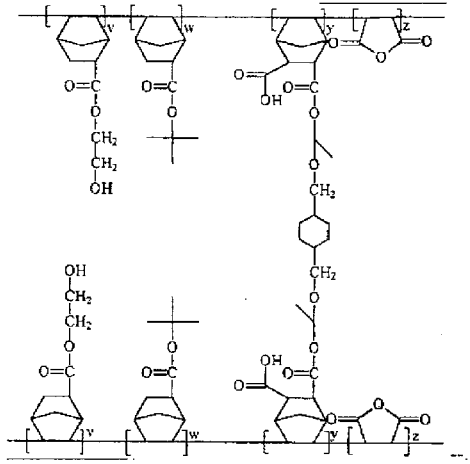

Column 19,
Line 62, before "wherein each" in claim 11, please add -- and mixtures thereof, --.

Column 21,
Line 9, before "(iv) maleic anhydride;" in claim 16, please add -- and mixtures thereof; and --.

Column 22,
Line 32, the "1.0%" in claim 23, should read -- 0.1% --.

Signed and Sealed this

Twenty-second Day of October, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,368,770 B1
APPLICATION NO. : 09/621125
DATED : April 9, 2002
INVENTOR(S) : Min Ho Jung et al.

Page 1 of 1

It is certified that error appears in the above-identified patent and that said Letters Patent is hereby corrected as shown below:

Column 10, line 39, the "butanedioldiethyether" should read --butanedioldiethylether--.
Column 20, line 18, the "propandioldiethylether" in claim 15 should read --propanedioldiethylether--.
Column 20, line 24, the "carboxlic" in claim 15 should read --carboxylic--.
Column 20, line 26, the "butanedioldiethyether" in claim 15 should read --butanedioldiethylether--.
Column 21, line 35, the "di-tert-buty" in claim 18 should read --di-tert-butyl--.
Column 22, line 25, the "hexafluorophsphate" in claim 22 should read --hexafluorophosphate--.

Signed and Sealed this

Twenty-seventh Day of February, 2007

JON W. DUDAS
*Director of the United States Patent and Trademark Office*